(12) United States Patent
Kerr

(10) Patent No.: US 10,413,285 B2
(45) Date of Patent: Sep. 17, 2019

(54) VASCULAR OCCLUSION DEVICE CONFIGURED FOR INFANTS

(71) Applicant: PFM MEDICAL, INC., Carlsbad, CA (US)

(72) Inventor: Marshall Kerr, Carlsbad, CA (US)

(73) Assignee: PFM MEDICAL, INC., Carlsbad, CA (US)

( * ) Notice: Subject to any disclaimer, the term of this patent is extended or adjusted under 35 U.S.C. 154(b) by 32 days.

(21) Appl. No.: 14/207,215

(22) Filed: Mar. 12, 2014

(65) Prior Publication Data

US 2014/0277095 A1 Sep. 18, 2014

Related U.S. Application Data

(60) Provisional application No. 61/778,045, filed on Mar. 12, 2013.

(51) Int. Cl.
*A61B 17/00* (2006.01)
*A61B 17/12* (2006.01)

(52) U.S. Cl.
CPC .... *A61B 17/0057* (2013.01); *A61B 17/12109* (2013.01); *A61B 17/12145* (2013.01); *A61B 2017/00345* (2013.01); *A61B 2017/00575* (2013.01); *A61B 2017/00592* (2013.01); *A61B 2017/00623* (2013.01); *A61B 2017/00628* (2013.01); *A61B 2017/00641* (2013.01); *A61B 2017/1205* (2013.01)

(58) Field of Classification Search
CPC ............... A61F 2/013; A61B 17/12109; A61B 17/12145
USPC .......................................................... 606/200
See application file for complete search history.

(56) References Cited

U.S. PATENT DOCUMENTS

| | | | | |
|---|---|---|---|---|
| 5,413,586 | A * | 5/1995 | Dibie et al. | 606/200 |
| 5,749,891 | A * | 5/1998 | Ken | A61B 17/12022 606/200 |
| 6,338,736 | B1 * | 1/2002 | Boosfeld | A61B 17/12022 606/191 |
| 2002/0151926 | A1 * | 10/2002 | Wallace | A61B 17/12022 606/200 |
| 2006/0079926 | A1 * | 4/2006 | Desai et al. | 606/200 |
| 2006/0116711 | A1 * | 6/2006 | Elliott | A61B 17/12022 606/200 |
| 2007/0239199 | A1 * | 10/2007 | Jayaraman | 606/200 |
| 2011/0295303 | A1 * | 12/2011 | Freudenthal | 606/200 |
| 2012/0215236 | A1 * | 8/2012 | Matsunaga | A61B 17/0644 606/151 |

* cited by examiner

*Primary Examiner* — Richard G Louis
(74) *Attorney, Agent, or Firm* — Donn K. Harms

(57) ABSTRACT

A microcatheter deliverable implant is provided formed of an elongated wire of a diameter capable of delivery through the axial passage of such a microcatheter. A first portion of the formed implant forms a coiled first section larger in diameter than an anomaly to be blocked. A second portion formed by the coiled wire engages the implant between the first and second portions to block communication of fluid through the anomaly.

17 Claims, 4 Drawing Sheets

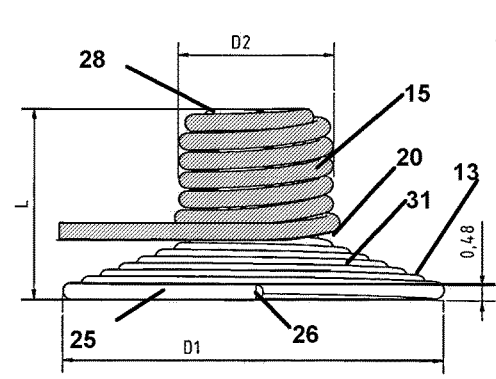
Fig. 2
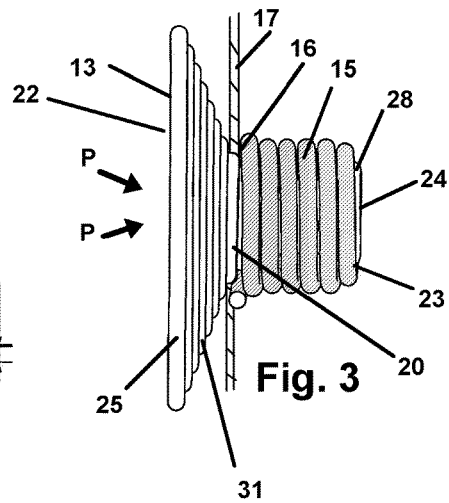
Fig. 3
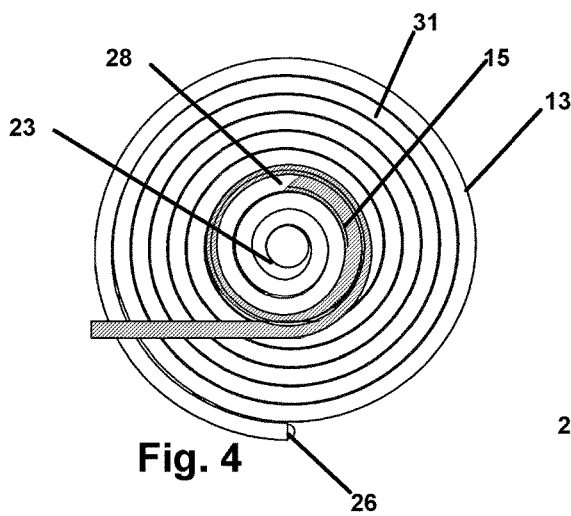
Fig. 4
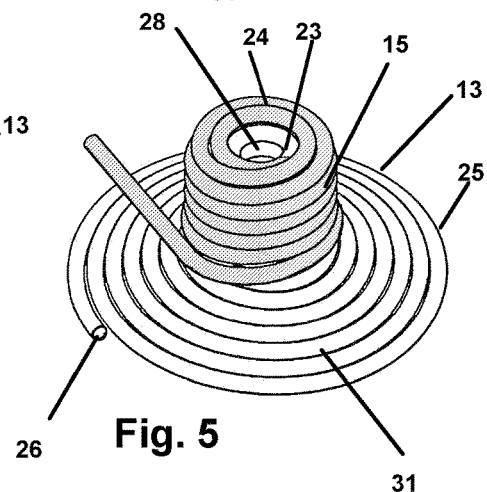
Fig. 5
| Configuration | D1 ±0,5 Ø-Distal (mm) | D2 ±0,5 Ø-Proximal (mm) | Elongated ±10 (mm) | L ±0,5 (mm) |
|---|---|---|---|---|
| 10x5 | 10 | 5 | 260 | 5,5 |
Fig. 6

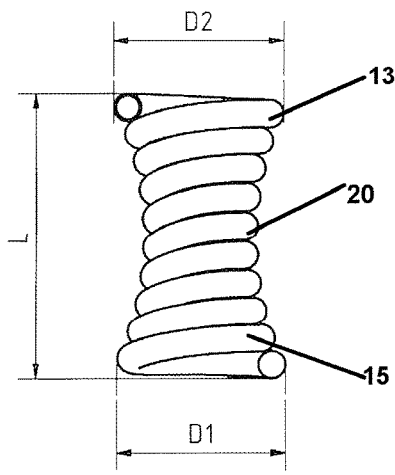
Fig. 7
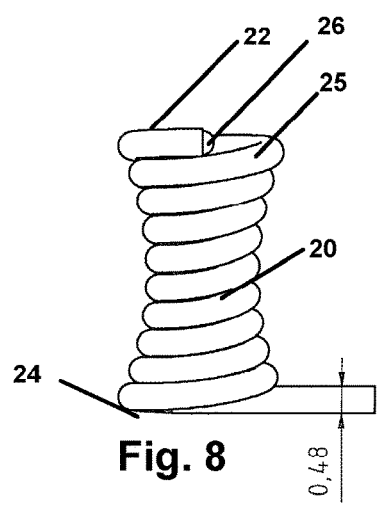
Fig. 8
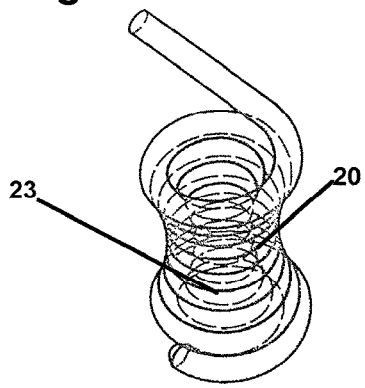
Fig. 9
| Configuration | D1<br>Ø-Distal (mm) | D2<br>Ø-Proximal (mm) | Elongated<br>(within catheter) | L<br>Length Deployed |
|---|---|---|---|---|
| 3x3 | 3 | 3 | 65 | 4,5 |
| 4x3 | 4 | 3 | 95 | 4,5 |
| 3x4 | 3 | 4 | 95 | 4,5 |
Fig. 10

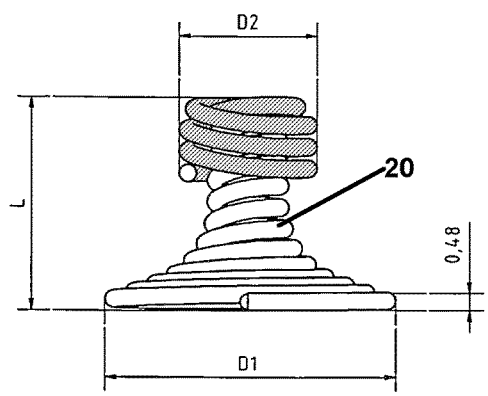
Fig. 11
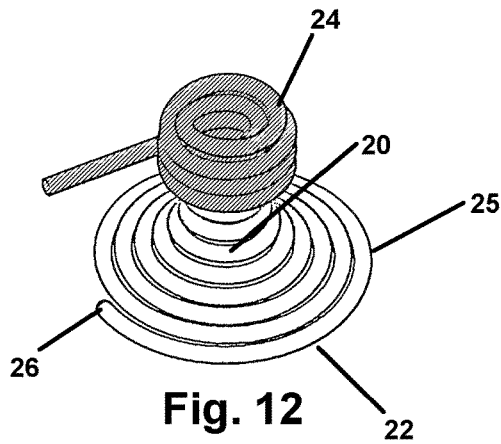
Fig. 12
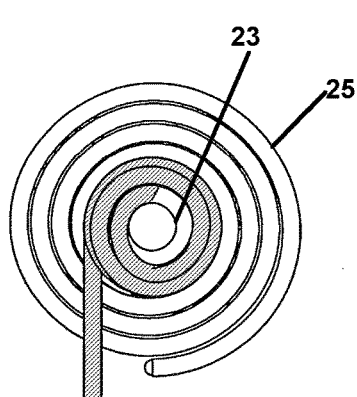
Fig. 13
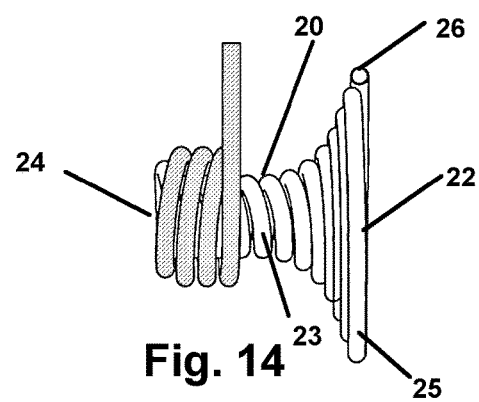
Fig. 14
| Configuration | D1 ±0.5<br>Ø-Distal<br>(mm) | D2 ±0.5<br>Ø-Proximal<br>(mm) | Elongated<br>±10 (mm) | L<br>Length<br>−0.5 (mm) |
|---|---|---|---|---|
| 7×4 | 7 | 4 | 160 | 5 |
Fig. 15

VASCULAR OCCLUSION DEVICE CONFIGURED FOR INFANTS

This application claims priority to U.S. Provisional Patent Application Ser. No. 61/778,045 filed on Mar. 12, 2013 and incorporated herein in its entirety by this reference thereto.

BACKGROUND OF THE INVENTION

1. Field of the Invention

The present invention relates to vascular occlusion devices employed for occluding vascular structures. More particularly the disclosed device and method relate to an occlusion device which is configured for implantation through the extremely narrow and serpentine vascular structures of newborns and infants where heretofore such devices were not employable. Further, the device provides a novel deployed implant especially configured to maintain a secure mount at the implant site which in infants and newborns is especially challenging due to the small nature of such sites and the thin and delicate surrounding tissue.

2. Prior Art

There are many instances in medicine where patients may have blood vessels and other unwanted vascular structures (sometimes man made structures) which need to be blocked or segregated from fluid passages of the vascular system, in order to treat the patient. Such devices may include stents or in a majority of cases where an occlusion of the site is desired, shaped metal coils are employed which, once released, provide a means for blocking an intended vascular passage.

Such metal coil implants are initially engaged in a catheter or delivery tube in a linear fashion and an elongated shape or configuration, in order for the shaped metal implant to follow the axial conduit within the catheter for implantation from the distal end of the catheter at the delivery site. Formed of coiled memory metal, the coils of the implant, upon deployment from the distal end of the catheter, wind to their original shape to form a blocking component configured to block or segregate a section of the vascular system desired from the adjacent system.

However, because such coil devices are delivered to a deployment site within these vascular structures with catheters, when the patient is an infant or newborn child, a severe problem arises. This is because when these vascular structures exist in very small children and infants, as well as in difficult to access parts of the body (as is the case for the brain, coronary arteries or other tortuous vessels in the abdomen), it becomes necessary that the coil-shaped implant be delivered by translation through the conduit of very small tubes called microcatheters.

However, because the physical requirements of the cross section of the axial conduit of such small microcatheters, conventionally sized and tensioned coil-shaped occlusion devices do not work well. Most implants have cross sections of the coil of the implant, which even in an elongated positioning of the wire forming the coil, exceed the diameter of microcatheter devices. Those that have a sufficiently narrow coil diameter to translate through the conduit of a microcatheter when deployed have not worked well in infants and children because they lack the tension on deployment for a secure engagement to the vascular or surrounding tissue. Such conventional devices of lower tension, in addition, have shapes which on deployment lack the ability to achieve a secure compressive engagement to occlude apertures in infants, such as between heart chambers, and remain engaged to the tissue surrounding the aperture being sealed.

Employment of such conventional coils can result in a dismounted coil for instance when deployed to seal a patent ductus arteriosus (PDA) in an infant or newborn who have high heart rates of 150 beats or more. In addition to the movement imparted by the heart beats, such infants have thin delicate tissue which must provide the engagement for the deployed implant. Such a dismount should it occur, is life threatening and requires immediate more invasive surgery to remove the dismounted implant which is additionally life threatening.

As such, there is a continuing unmet need for catheter-delivered implant capable of translation and delivery through a microcatheter which is required in the treatment of infants and newborns and in very small vascular system areas in adults. Additionally, such a device, on deployment, must achieve the desired occlusion and concurrently a secure engagement to the tissue of the patient, in high blood flow areas which impart extra force against the implant which can lead to dislodgement.

The present invention solves the shortcomings of the current art, in providing a vascular occlusion coil-type implant which can be delivered via translation through a microcatheter for implantation in infants and newborns and small blood vessels. The disclosed device in such a communication through the axial passage of a microcatheter, once deployed and engaged with patient tissue, provides the desired occlusion for very high flow vascular structures. The disclosed device accomplishes these tasks, using a coil which is coiled to extremely high tension resistance to coil-elongation to a substantially straight configuration elongated for translation through a microcatheter by hand pushing on the control wire, or using a pushing component engaged to the proximal end of the catheter to push on the control wire.

Further, once released, the coil device herein assumes an overlapping conical shape at one end which forms a particularly secure mount when a second end of the coil reverses on deployment to cover the narrow end of the first deployed end. As noted, once deployed from a microcatheter, the unique shape and overlapping configuration of the deployed coiled implant, provides the requisite strength to block an area of high blood flow and resulting high pressure forces. Further, the unique overlapping coiled configuration achieves the necessary engaging compressive force against surrounding tissues to maintain a permanent mount in the patient and thus avoid a life-threatening dismount.

The forgoing examples of related art and limitation related therewith are intended to be illustrative and not exclusive, and they do not imply any limitations on the invention described and claimed herein. Various limitations of the related art will become apparent to those skilled in the art upon a reading and understanding of the specification below and the accompanying drawings.

SUMMARY OF THE INVENTION

The device herein disclosed and described provides a solution to the shortcomings in prior art and achieves the above noted goals through the provision of an intravenous microcatheter deliverable coiled implant. The coiled implant is especially configured for employment in the many instances where infants with narrow blood vessels, require a device to prevent cross fluid flow in a very high blood flow area.

The memory metal formed coiled implant herein is formed with metal in a manner yielding very high tension on deployment as well as sufficiently low pressure on the interior conduit of the microcatheter used for translation of the coil to the implant site.

With the unique coil-over-coil deployed configuration of the high tension coiled implant herein, the present device is able to occlude both small and large unwanted vascular structures. However, even though the implant achieves a size and engagement to block a large area, and its unique frusto-conical wrap-over configuration concurrently provides a stable and strong mount, it still may be elongated to an enlarged configuration where it is deliverable by way of a microcatheter.

Because of the size and lack of sufficient prior art engagement structures to be used in narrow vascular structures of infants, and to remain mounted even if deployable therethrough, many of such vascular deformities such as certain coronary artery fistulas and PDAs in premature infants and newborns and children, are currently unable to be corrected using a minimally invasive transcatheter type surgical procedure. Thus, patients most in need of the most non-invasive care, newborn children and infants, have instead been subjected to more conventional surgery which is not well tolerated by adults, let alone children. Further, while other lesions can be treated with a variety of other larger low tension coils and plugs the disclosed device herein renders many of these types procedures easier.

The unique shape and high radial force of the coils herein described and shown, provide an implant which enables surgeons to perform a transcatheter type procedure on newborns and infants, rather than more invasive surgical procedures being used. Further, the high degree of control of the implant during and on release, and the ability of the high tension coiled implants to translate through microcatheters, provides such surgeons with a high degree of control and confidence the deployed coil will be in the proper position and will stay mounted after deployment.

The disclosed coiled implant, developed with extensive experimentation, has a wire cross sectional size configured to be delivered via the axial conduit of conventional microcatheters which are designed specifically for the treatment of high flow vascular lesions. The current device is formed in a rigorous, high radial force coil, which has a radial force much higher than currently available 0.025-0.027 coils. Radial force in experiments with the device herein, and with various prior art implants, is meant the amount of force required to force the device, in its elongated position, from the distal end of the delivery catheter, and into its coiled deployed shape. This measurement appears to correlate to the amount of force the coils of the deployed device provide in resisting movement of the adjacent coils away from each other. While other prior art coiled devices which were larger in diameter required just 0.2 newtons to draw the elongated component from within an axial pathway such as that of a catheter, the device herein required 0.3 newtons for such an extraction to the deployed position. This is a 50% higher amount of force required to draw the device in its elongated mode within an axial passage of a catheter, into the deployed overlapped cone shape. An equally larger amount of force is required to deflect or dislodge the coils of the device herein, from their memory position in an overlap of coiled sections.

The device is able to track through a microcatheter and upon reaching the implant site it has a highly controlled release. Because the higher tensional force of the device imparts a high frictional force against the microcatheter axial wall, the system provides a pushing mechanical mechanism designed to aid the surgeon in pushing the wire and coil through the catheter in case the microcatheter has kinks, which frequently happens. Upon deployment the memory metal of the implant, the resulting high radial force maintaining the coils adjacent to each other, forms a coil shape designed specifically for occlusion in infants and newborns using a unique second portion of the coil over a first-deployed portion of the coil configuration.

With respect to the above description, before explaining at least one preferred embodiment of the herein disclosed coiled implant invention in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other structures, methods and systems for carrying out the several purposes of the present disclosed coiled implant device. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Objects, features, and advantages of the invention will be brought out further in the following part of the specification, wherein detailed description is for the purpose of fully disclosing the invention without placing limitations thereon.

BRIEF DESCRIPTION OF DRAWING FIGURES

The accompanying drawings, which are incorporated herein and form a part of the specification, illustrate some, but not the only or exclusive, examples of embodiments and/or features. It is intended that the embodiments and figures disclosed herein are to be considered illustrative rather than limiting. In the drawings:

FIG. 1a shows the particularly favored shape of the coiled implant on deployment to an as-used configuration, yielding a second portion of the coil reversing coil direction to encircle over a first portion of the coil, thereby providing an especially secure mount and ability to occlude larger areas.

FIG. 2 shows the different dimension measurements of currently favored coiled implants.

FIG. 3 depicts the device of FIG. 1 in an as-used position occluding an unwanted peripheral arterial or venous structures wherein the large diameter first-deployed end of the device, is positioned on the pressure side of the occlusion.

FIG. 4 shows the device of FIG. 1a from an overhead view showing the reverse coil of the second portion of the device over the axial cone rising from the base of the first portion.

FIG. 5 depicts an isometric view of the implant device of FIG. 4, showing the large diameter first portion of the deployed implant which rises in a core in a central area and which is subsequently overlapped by a second portion of the implant during deployment.

FIG. 6 is a chart showing the measurements of one preferred mode of the device of FIG. 2, where the diameter of the smaller end is half that of the larger or first portion of the device.

FIG. 7 is another mode of the device having opposing end diameters which vary from equal to 25% more or less than equal.

FIG. 8 shows another view of FIG. 7.

FIG. 9 depicts a view of the device of FIG. 7 showing the overlapping reverse exterior coil construction of the deployed device, which is common to all modes.

FIG. 10 depicts a chart of the diameters of the various configurations of the device in the mode of FIG. 7.

FIG. 11 depicts another mode of the device which has a first end having diameter 1.75 times that of the second end of the deployed device.

FIG. 12 shows the device of FIG. 11 being deployed wherein the shaped memory material deploys in a first portion to form the large diameter section with central core axial winding rising from the center which are overlapped by the second section.

FIG. 13 depicts an overhead view of the device of FIG. 12 showing the axial core windings rising from the center of the base of the first portion, which are then overlapped by the second portion.

FIG. 14 is a side view of FIG. 13.

FIG. 15 depicts some preferred measurements of this mode of the device and ratios of similar modes.

DETAILED DESCRIPTION OF THE PREFERRED EMBODIMENTS OF THE INVENTION

Figure 1:
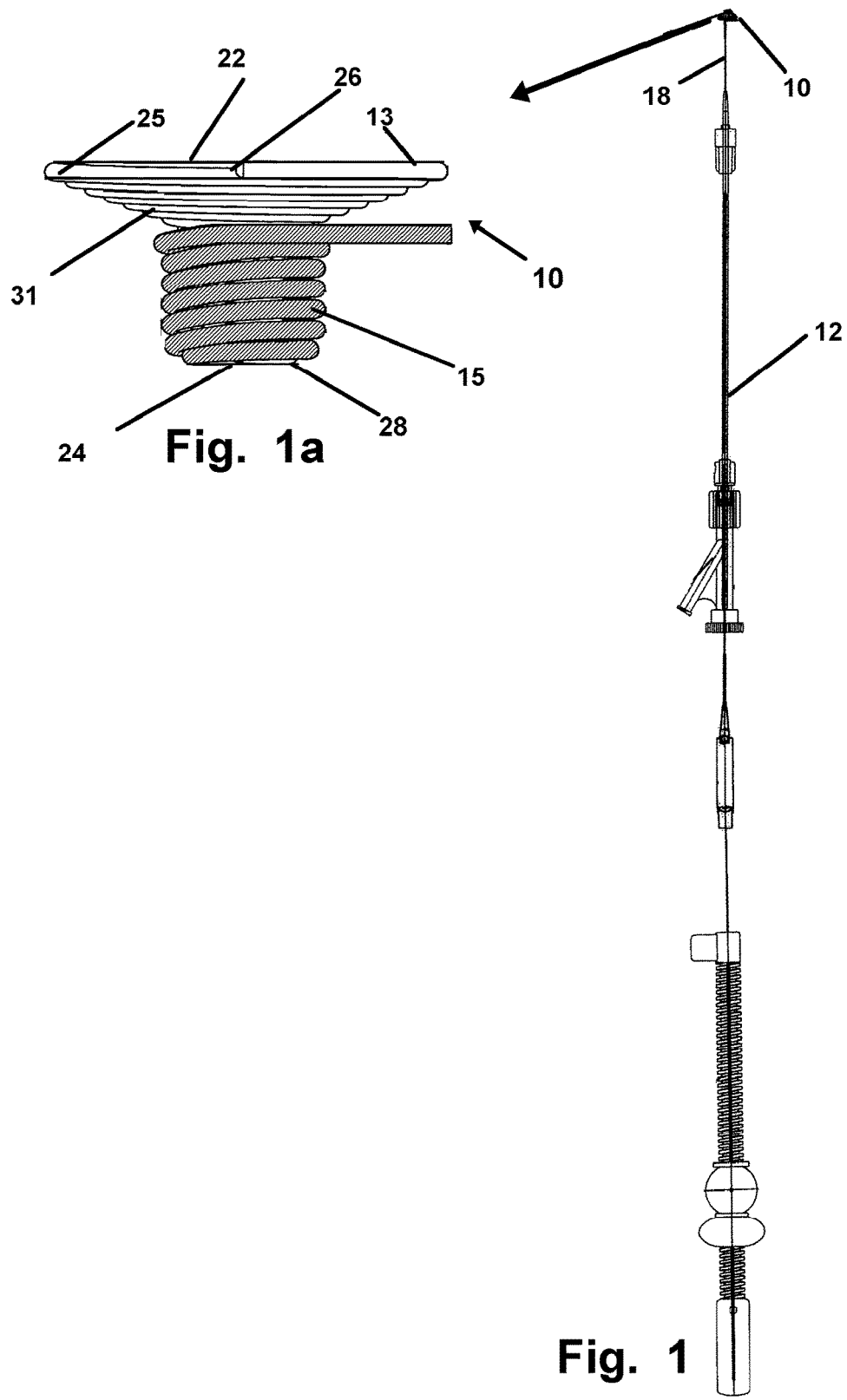
FIG. 1 shows a view of the microcatheter device herein deployed at the end of a control wire in a deployment system having a pushing component on a proximal end, and the unique coiled implant extending from the distal end.

In this description, the directional prepositions of up, upwardly, down, downwardly, front, back, top, upper, bottom, lower, left, right and other such terms refer to the device as it is oriented and appears in the drawings and are used for convenience only; they are not intended to be limiting or to imply that the device has to be used or positioned in any particular orientation.

Now referring to drawings in FIGS. 1-15, wherein similar components are identified by like reference numerals, there is seen in FIG. 1, a view of the microcatheter 12 having an axial passage through which the implant device 10 herein is sized for passage, in an elongated state to an implant site. At the implant site, the device 10 will achieve a deployed configuration as in FIG. 2, 7, or 11 or other deployed configuration where a first portion 13 of the implant device 10, deploys on a first side of an aperture or opening or other vascular or arterial area to be blocked, and a second portion 15 of the implant device 10 coils around a coiled mid portion extending away from the first portion 13.

Translation through the axial passage of the catheter 12 type device is accomplished using a control wire 18. The wire 18 is translated through the axial passage of the catheter 12 to the distal exit to first extend the first portion 13 of the implant device 10 on a first side of the aperture 16 or passage, or opening to be blocked such as shown in FIG. 3. The first portion 13 shown in FIG. 3, which is also the distal end 22, and as is the case with all modes of the device 10, assumes its memorized shape as the wire forming the device 10 translates from the catheter and coils.

In filling or plugging unwanted vascular or arterial anomalies such as anomalies of origin, termination, structure, or course, such as coronary artery fistulas, and PDA's, especially in infants, the device 10 in deployed configuration, outside of the catheter 12, achieves a coiled shape, to form a narrow mid section 20 in a central area of the formed implant device 10, between the distal end 22, and proximal end 24 or second portion 15 of the device 10, which is removably engaged to release from the control wire 18. This centrally located narrow mid section 20, in combination with the large end section 25 on the pressurized side of the anomaly being filled, fills or plugs the unwanted aperture 16 or passage or recess or other communicative anomaly in the vascular or arterial structure.

As depicted in FIGS. 2-5 and 22-14, a particularly preferred mode of the device 10 forms the shape of the distal end 22 or first portion 13 of the device 10 to deploy, which is coiled to form a semi-planar distal end section 25 which is formed by inward coils from a perimeter edge starting at a distal endpoint 26 of the wire. During deployment of the first portion 13 to form the end section 25, the wire coils inward to a central section 27, wherein the coils rise in an axial winding 23 extending away from the formed end section 25 forming the first portion 13 of the device 10.

During deployment of the first portion 13 of the device 10, at a peak 28 distance of the axial winding 23, from the end section 25, the shaped metal wire reverses course. The surgeon at this point can check with a camera or visualization means to determine if the end section 25 is of sufficient diameter to block the intended anomaly or aperture 16 as referred to herein. If such is the case, the second section 15 may be formed by the wire extension from the distal end of the catheter 12, which winds back toward the end section 25 by a winding around the axial winding 23 formed by the wire between the peak 28 of the windings forming the end section 25. This second section 15 forms a diameter of the device 10 on the opposing side of the aperture 16 or other anomaly which prevents dislodgement toward the end section 25, and positions the device 10 in an operative engagement deployed with the intended anomaly such as the depicted aperture 16 in tissue 17 between two arterial or vascular conduits.

As shown in all modes of the device 10 a first portion 13 having an end section 25 formed substantially larger in diameter than the diameter at the proximal end 24 is particularly preferred. This is because as shown in FIG. 3, allowing the wire to first communicate through the aperture 16 whereupon in a deployment of the first portion 13 the wire winds to form an end section 25 substantially wider than the diameter of narrow mid area 20 the central area of the device 10 allows the end section 25 to be tested on the pressurized side "P" in FIG. 3, and allows the mid area 20 to extend to substantially fill the aperture 16 or anomaly between two arterial and/or vascular conduits in the body. When placing the end section 25 on the side of the aperture 16 which has fluid pressure P, the fluid contacting the end section 25, pushes the end section to contact the area of tissue 17 surrounding the communicative anomaly shown as the aperture 16 and substantially prevents fluid flow between the two vascular or arterial passages.

As can be seen in FIGS. 5, 9, and 13 for instance, once the first portion 13 is deployed to form to the end section 25, the wire of the formed device 10 follows windings along axial windings 23 to form a center area communicating through the anomaly such as the aperture 16. At a peak 28 of the axial windings 23 extending a distance from the end section 25, the memory metal wire, such as Nitinol, is pre-shaped to reverse the wind direction, back over the axial winding 23 toward the aperture 16 and end section 25. This reverse winding of the second section 15, renders an area of the device 10 on the un pressurized side of the anomaly or aperture 16, wider than the aperture 16 to prevent dismount from the tissue 17 and passage in the opposite direction. This double wind of the wire, in all modes of the device 10, over the axial winding 23, thus renders the device 10, anchored in patient tissue.

However, at any time prior to disengagement of the device 1—from the guide wire 18, it may be retrieved back into the axial passage of the catheter 12. This gives the user, or surgeon, the ability to test the size of the end section 25 of the first portion 13 deployed, and insure that it is sufficiently wide in diameter, to plug the anomaly such as the aperture 16 or hole, or gap, or other unwanted arterial or vascular passage, prior to release of the second portion 15. Since the larger end section 25 of the first portion 13, will be on the pressurized side of the aperture 16, is pushed against the tissue surrounding it by the pressurized fluid and prevent leakage or back flow through the anomaly such as the aperture 16. Using means for depicting the implant site, the surgeon may determine the proper size of the end section 25, prior to continued deployment.

As noted FIG. 1a as well as 2-5 and 11-14, shows the particularly favored shapes of the coiled implant device 10 on deployment to an as-used configuration. As depicted, the end section 25 in the first portion 13, assumes an upward angle or conical shape as the wire winds from a perimeter to a center area. This inclined surface 13 is preferred as testing has shown it better allows the surface 31 of the end section 25 to self-fit against the tissue 17 and anomaly which is not necessarily circular or even in shape, and allows portions of the surface 31 to fit against tissue surrounding the anomaly such as the aperture 16 for a good seal.

The axial windings 23 during deployment, rise from the surface 31 to the peak 28 and will provide a means to self-center the device 10 with and through the anomaly such as an aperture 16 and placing the surface 31 in communication with flesh 17 around it. So positioned, with the axial windings communicating through the anomaly, in all modes of the device 10, the reverse wire windings forming the second portion 15 of the device 10, in a reversing direction to encircle over the axial windings 23 of the first portion 13 of the implant device 10, thereby provide an especially secure mount and ability to occlude larger areas.

FIGS. 2-5 shows different views of the device 10 of FIG. 1a, and shows the diameter D1 at a distal end forming the end section 25 of the first portion 13 of the device, and a diameter D2 of the proximal end or second portion 15 of the device 10 of FIGS. 3-5. A currently preferred configuration of the device 10 of FIGS. 2-5 is with a diameter D1 of 10 mm plus or minus 0.5 mm, and a diameter D2 being ½ the diameter of D1 or 5 mm plus or minus 0.5 mm which is depicted in FIG. 6.

FIGS. 7-9 show another mode of the device 10 having opposing diameters D1 at a first portion 13 of the device and D2 at the second portion 25 of the device 10, which vary from being substantially equal in size, to having one of the respective opposing sides being 25% more than the other which is shown in FIG. 10.

FIGS. 11-14 depicts another mode of the device 10 which has a first portion 13 defining the end section 25 has a first Diameter D1, and said second portion second has a diameter d2 which is substantially 1.75 times that of the second end of the second portion 15 of the device 10 in a deployed state. Again the surface 31 of the end section 25 is conical and rises at an angle from a low point at the perimeter of end section 25 to a high point in a center of the end section 25 where the axial windings 23 begin. In one preferred set of dimensions following this ratio, the diameter D1 is 7 mm and the diameter of D2 is 4 mm as shown in FIG. 15. Although other configurations following this ratio may be employed so long as the incline of the surface 31 is provided toward a center such as also is done in FIGS. 2-5.

Thus while experimentation has shown the above noted modes of the device 10 have defined measurements to the first portion and second portion diameters, which work best, other modes work well also where the first portion 13 defining the end section 25 has a diameter from 1.5 to 2.5 times the second diameter defined by the diameter of the second portion 15.

This invention has other applications such as in small blood vessels of the brain of adults, as well as others, and those skilled in the art upon reading this disclosure and being educated with regard to this device and method could discover such modes of employment and such are anticipated within the scope of this application. Further, the explanation of the features of this invention does not limit the claims of this application, and other applications developed by those skilled in the art are considered to be included in this invention.

It is additionally noted and anticipated that although the device is shown in its most simple form, various components and aspects of the device may be differently shaped or slightly modified when forming the invention herein. As such those skilled in the art will appreciate the descriptions and depictions set forth in this disclosure or merely meant to portray examples of preferred modes within the overall scope and intent of the invention, and are not to be considered limiting in any manner.

While all of the fundamental characteristics and features of the invention have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention or claims herein. Consequently, all such modifications and variations and substitutions are included within the scope of the invention as defined by the following claims.

What is claimed is:

1. A microcatheter deliverable implant, comprising: an elongated wire formed of memory material; said wire translatable through a distal end of an axial conduit for a deployment within an anomaly at an implant site; a coiling of said wire during said deployment, forming a distal semi-planar or frusta Conical first section of said implant having a first diameter; said wire extending from a central portion of said first section, in a first portion defined by a first helical winding of adjacent substantially parallel coils of said wire, extending in a first direction a distance from said first section to a proximal end of said first portion; at said proximal end of said first portion, a second portion of said implant formed by said wire reversing direction from said first direction to a second direction in a second helical winding of substantially parallel adjacent coils of said wire, overlapping said first helical winding, said second helical winding extending in said second direction from said proximal end of said first portion to a compressive communication at a second end of said second helical winding against said central portion of said first section; said second portion of said implant defining a second diameter of said implant running between said proximal end of said first portion and said first section, said second diameter being smaller than said first diameter; both the first diameter and the second diameter are configured to prevent dismounting of the implant; and said implant in said deployment, configured for positioning said first section of said implant on a first side of said of an anomaly in a blood circulation system of a patient with said second portion of said implant configured to be located on a second side of said anomaly, said compressive communication of said second end of said second helical winding against said first section configured to form a compressive sandwiched engagement of said implant with said first and second sides of said anomaly defining a barrier blocking blood flow between said first side and said second side of said anomaly.

2. The implant of claim 1, wherein said wire is retractable from said deployment back into said axial passage.

3. The implant of claim 1, additionally comprising:
said first section formed by a spiral coiling of said wire extending from a first coil defining a first perimeter of said first section, to said central portion of said first section;
said first perimeter defining said first diameter of said implant.

4. The implant of claim 3, additionally comprising:
said first section having a first surface, said first surface configured for a centering of said implant with said anomaly during said deployment, prior to a formation of said sandwiched engagement therewith.

5. The implant of claim 4 additionally comprising:
said first diameter being sized between 1.5 and 2.5 times said second diameter.

6. The implant of claim 5, wherein said first diameter is sized 1.75 times said second diameter.

7. The implant of claim 5, wherein said first diameter is double said second diameter.

8. The implant of claim 3 additionally comprising:
said first diameter being sized between 1.5 and 2.5 times said second diameter.

9. The implant of claim 8, wherein said first diameter is sized 1.75 times said second diameter.

10. The implant of claim 8, wherein said first diameter is double said second diameter.

11. The implant of claim 1 additionally comprising:
said first diameter being sized between 1.5 and 2.5 times said second diameter.

12. The implant of claim 11, wherein said first diameter is sized 1.75 times said second diameter.

13. The implant of claim 12 wherein said first section is adapted for positioning upon a side of said anomaly having fluid pressure therein, whereby said first diameter prevents said fluid pressure forcing said implant through said anomaly.

14. The implant of claim 11, wherein said first diameter is sized 1.75 times said second diameter.

15. The implant of claim 14 wherein said first section is positionable upon a side of said anomaly having fluid pressure therein and said first diameter provides means to prevent forcing of said implant through said anomaly.

16. The implant of claim 11 wherein said first section is adapted for positioning upon a side of said anomaly having fluid pressure therein, whereby said first diameter prevents said fluid pressure forcing said implant through said anomaly.

17. A high radial force coil implant, comprising:
an elongated wire formed of memory material capable of yielding a very high tension on deployment and low pressure on an interior of an axial conduit;
said wire translatable through a distal end of said axial conduit for a deployment within an anomaly at an implant site;
a coiling of said wire during said deployment, forming a distal semi-planar or frusto-conical first section of said implant having a first diameter;
said wire extending from a central portion of said first section, in a first portion defined by a first helical winding of adjacent substantially parallel coils of said wire, extending in a first direction a distance from said first section to a proximal end of said first portion;
at said proximal end of said first portion, a second portion of said implant formed by said wire reversing direction from said first direction to a second direction in a second helical winding of substantially parallel adjacent coils of said wire, overlapping said first helical winding,
said second helical winding extending in said second direction from said proximal end of said first portion to a compressive communication at a second end of said second helical winding against said central portion of said first section, said second helical winding remaining proximal to said first section;
said second portion of said implant defining a second diameter of said implant running between said distal end of said first portion and said first section;
both the first diameter and the second diameter are configured to prevent dismounting of the implant; and
said implant in said deployment, configured for positioning said first section of said implant on a first side of said of an anomaly in a blood circulation system of a patient with said second portion of said implant configured to be located on a second side of said anomaly, said compressive communication of said second end of said second helical winding against said first section configured to form a compressive sandwiched engagement of said implant with said first and second sides of said anomaly defining a barrier blocking blood flow between said first side and said second side of said anomaly.

* * * * *